(12) United States Patent
Pastor

(10) Patent No.: US 8,974,742 B2
(45) Date of Patent: Mar. 10, 2015

(54) DEVICE FOR PHOTOCATALYTIC TREATMENT OF FLUIDS

(75) Inventor: Jean-Pierre Pastor, Caracas (VE)

(73) Assignee: Aclorve S.A.S., Paris (FR)

( * ) Notice: Subject to any disclaimer, the term of this patent is extended or adjusted under 35 U.S.C. 154(b) by 163 days.

(21) Appl. No.: 12/682,220

(22) PCT Filed: Sep. 30, 2008

(86) PCT No.: PCT/IB2008/053984
§ 371 (c)(1),
(2), (4) Date: Apr. 8, 2010

(87) PCT Pub. No.: WO2009/047668
PCT Pub. Date: Apr. 16, 2009

(65) Prior Publication Data
US 2010/0209312 A1 Aug. 19, 2010

(30) Foreign Application Priority Data

Oct. 8, 2007 (EP) ..................... 07019639

(51) Int. Cl.
*B01J 19/08* (2006.01)
*A61L 9/20* (2006.01)

(52) U.S. Cl.
CPC ..................... *A61L 9/205* (2013.01)
USPC ..................... 422/186.3; 422/186; 210/748.1; 210/748.01; 210/748.14

(58) Field of Classification Search
CPC ..................... A61L 9/205
USPC ............. 422/186.03, 186; 210/748.1, 748.01, 210/748.14
See application file for complete search history.

(56) References Cited

U.S. PATENT DOCUMENTS

| | | | | |
|---|---|---|---|---|
| 3,925,248 A * | 12/1975 | Moroni et al. | ................. | 502/159 |
| 5,112,370 A | 5/1992 | Gazzano | | |
| 5,817,276 A | 10/1998 | Fencl et al. | | |
| 6,589,489 B2 * | 7/2003 | Morrow et al. | ............ | 422/186.3 |
| 7,326,090 B2 * | 2/2008 | Cayzac | ......................... | 439/680 |
| 2002/0081246 A1 | 6/2002 | Tsukada et al. | | |
| 2002/0081257 A1 * | 6/2002 | Burke et al. | ................. | 423/248 |
| 2003/0003304 A1 * | 1/2003 | Ohtsu et al. | ................... | 428/412 |
| 2004/0007453 A1 * | 1/2004 | Scahill et al. | .............. | 204/157.3 |
| 2005/0008549 A1 | 1/2005 | Hsu | | |
| 2005/0008861 A1 * | 1/2005 | Yadav et al. | .................. | 428/403 |
| 2007/0283961 A1 * | 12/2007 | Hsieh | ........................ | 128/205.29 |
| 2009/0004046 A1 * | 1/2009 | McEllen | .......................... | 422/2 |

FOREIGN PATENT DOCUMENTS

CN 1843513 A 10/2006
DE 909292 4/1954

(Continued)

*Primary Examiner* — Xiuyu Tai
(74) *Attorney, Agent, or Firm* — Faegre Baker Daniels LLP

(57) ABSTRACT

A reactor unit for photocatalytic treatment of fluids such as air, includes a catalyzer device (4) comprising a catalytic material support having a generally tubular shape defining a fluid flow channel extending around and along a fluid flow path and a photocatalytic material coated on at least a portion of an internal surface of the support, and a radiation source (30) received in a central portion of the catalyzer device. The catalytic material support comprises a wall portion and a plurality of tapered protrusions (8) extending from an internal surface of the wall portion to a tip proximate to the radiation source, the tapered protrusions being arranged around the radiation source and along the fluid flow channel.

20 Claims, 7 Drawing Sheets

(56) References Cited

FOREIGN PATENT DOCUMENTS

| | | |
|---|---|---|
| EP | 0403984 A1 | 12/1990 |
| EP | 0470518 A1 | 2/1992 |
| EP | 0993859 A1 | 4/2000 |
| EP | 1426065 A1 | 6/2004 |
| EP | 1688151 A1 | 8/2006 |
| EP | 1790410 A1 | 5/2007 |
| EP | 1792632 A1 | 6/2007 |
| GB | 2405463 A | 3/2005 |
| JP | 2000279761 A | 10/2000 |
| JP | 2002-058728 * | 2/2002 |
| WO | 0170396 A2 | 9/2001 |

* cited by examiner

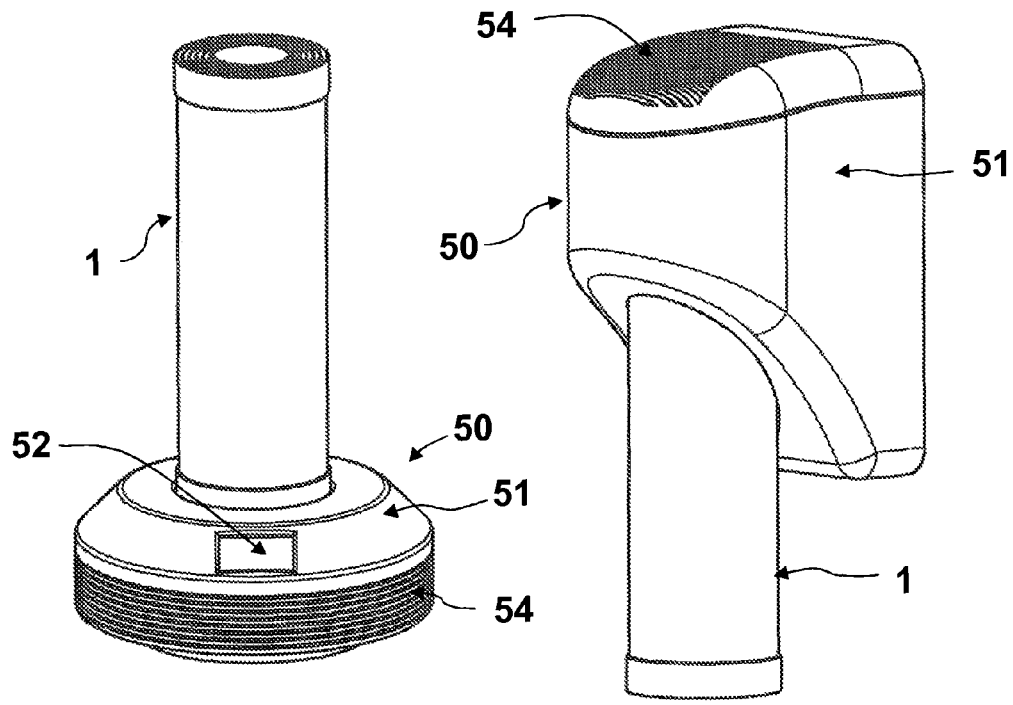
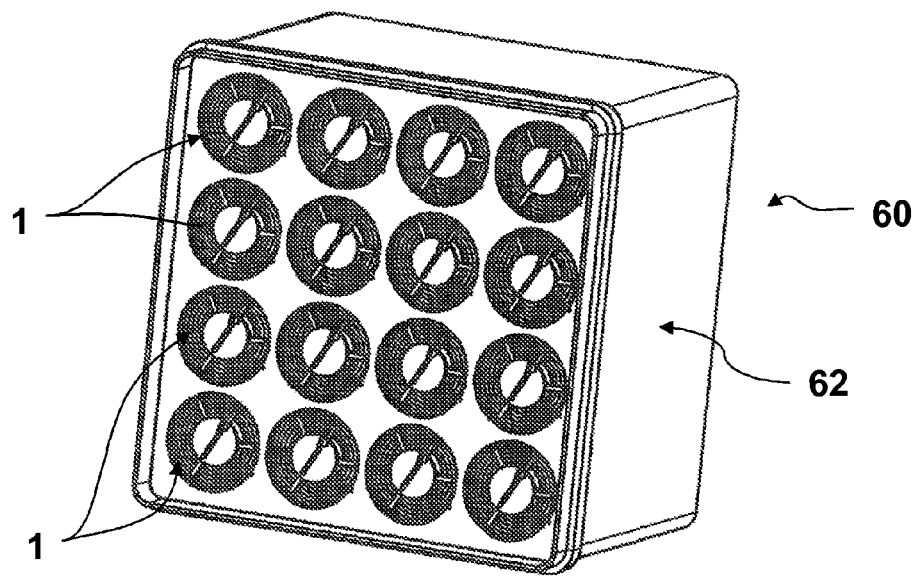
Fig. 8a
Fig. 8b
Fig. 8c

DEVICE FOR PHOTOCATALYTIC TREATMENT OF FLUIDS

BACKGROUND

The present invention relates to the field of devices for photocatalytic treatment of fluids, for instance for cleaning, deodorizing and sterilizing gases such as air.

Numerous air purification systems have been described, or are commercially available, which aim to remove various pollutants, such as dust, micro-particles, noxious gases, allergens, and pathogenic micro-organisms from the air. In the known systems, dust and other micro-particles are generally removed from the air by the use of filters. It is known to remove certain volatile and reactive molecules by the use of catalytic processes. The use of ultraviolet light radiation to inactivate certain micro-organisms is also described. It is known to combine the use of ultraviolet light and photocatalytic processes to accelerate the degradation of noxious particles and the destruction of micro-organisms.

The use of photocatalysts in devices for deodorising or purifying air is described in a number of patent applications, for example, U.S. Pat. No. 5,670,126, U.S. Pat. No. 6,558,639, US 2002/094298, U.S. Pat. No. 6,358,374, US 2004/007453, JP 11226357, WO 02/085989, and FR 2821558. The most common photocatalytic compound used in the known systems is titanium dioxide because of its excellent photocatalytic activity when irradiated with ultraviolet radiation, and its harmlessness to the human organism.

The photocatalyst is generally combined with a binder to form a photocatytic coating material. A photocatalytic material which is convenient to use, adheres well to a number of surface and may be applied to articles which do not support high temperatures is described in WO 2006/010993, hereby incorporated herein by reference. The photocatalytic material described in WO 2006/010993 comprises an inorganic binder including ultraviolet light permeable polymeric molecules, particularly acrylic molecules, a polar diluent, and particles of an inorganic semi-conductor, such as cadmium sulphide, zinc sulphide or titanium dioxide.

In known systems the photocatalytic material is generally coated on a filter element or other surfaces of the air purifying system irradiated by an ultraviolet light source, typically an ultraviolet lamp. For example EP 0978690 and WO 96/37281 describe systems in which air is passed through an air-permeable sheet supporting a photocatalytic material and placed in the vicinity of an ultraviolet light source. Such systems generally provide only limited air cleaning properties with respect to removing certain airborne pollutants, allergens and pathogens.

A system with improved air cleaning properties is described by WO 2007/060520, in which a photocatalytic material is coated on an inside surface of a tubular air conduit containing a UV lamp. A number of spaced apart blades are located on the inside surface of the air conduit in order to increase the surface area of photocatalytic material in the air conduit and to create turbulent flow of the air through the conduit.

EP 0470518 describes a system designed for the decomposition of organic substances in which a liquid is passed through a stainless steel reaction vessel containing an ultraviolet immersion lamp. According to EP 0470518 baffles are located on the inner surface of the stainless steel tube to cause turbulence in the flow of the liquid on the reaction vessel inner surface.

The known systems do however present a number of drawbacks. For instance the known systems are generally relatively complex and costly to manufacture and/or maintain. Moreover, the known systems either do not effectively treat all the air passing through the device, and/or cause excessive resistance on the air passing through with the consequence of increased noise and the need to employ more powerful fans for a given rate of airflow.

There is also an ongoing need for air purification systems which reliably and effectively remove, destroy or inactivate airborne pollutants, allergens and pathogens.

SUMMARY

It is an object of this invention to provide a device for use in the photocatalytic treatment of fluids which provides reliable and effective treatment of said fluids and which is economic to manufacture.

It would be advantageous to provide a reactor unit which provides reliable and effective cleaning, deodorizing and sterilizing of air and which is economic to manufacture.

It would be advantageous to provide an apparatus for the photocatalytic treatment of fluids that has a low pressure loss for a given rate of treated fluid flow.

It would be advantageous to provide an apparatus for the photocatalytic treatment of fluids that has low noise emission.

It would be advantageous to provide an apparatus for the photocatalytic treatment of fluids that is easy to use and versatile.

It would be advantageous to provide an apparatus for the photocatalytic treatment of fluids that is economic to manufacture, maintain and use.

It would be advantageous to provide an apparatus that can conveniently and effectively be used in the photocatalytic treatment of large volumes of fluids.

Objects of the present invention are achieved by a reactor unit according to claim 1.

Disclosed herein is a reactor unit for photocatalytic treatment of fluids including a catalyser device comprising a catalytic material support having a generally tubular shape defining a fluid flow channel extending around and along a fluid flow path and a photocatalytic material coated on at least a portion of an internal surface of the support, and a radiation source received in a central portion of the catalyser device. The catalytic material support comprises a wall portion and a plurality of tapered protrusions extending from an internal surface of the wall portion to a tip proximate to the radiation source, the tapered protrusions being arranged around the radiation source and along the fluid flow channel.

The term "proximate" as used in the present application is meant within a range of 0 (i.e. touching) to a distance of less than 50% the distance separating the surface of the radiation source and the internal surface of the catalytic device wall portion. The tips of the tapered protrusions may be located at a position within a range of 0 (i.e. touching the surface of the radiation source) to a distance of less than 50%, preferably less than 30%, the distance separating the surface of the radiation source and the internal surface of the catalytic device wall portion. For instance, the extremity of the tips of one or more tapered protrusions may be located at a distance within a range of 0 to 20 mm from an external surface of the radiation source, preferably within a range of 0 to 10 mm, more preferably within a range of 2 to 5 mm.

Advantageously the provision of a tubular catalytic material support with a plurality of tapered protrusions extending from a wall portion of the catalytic material support to a tip proximate to the radiation source not only provides a greatly increased surface area of photocatalytic material inside the reactor unit, but also increases the proportion of the coated internal surface of the catalyser device that is exposed to direct ultraviolet light from the radiation source.

The plurality of tapered protrusions arranged around the inner periphery of the generally tubular support and along its length in the fluid general flow direction also provide a plurality of meandering paths for the fluid flow, thus increasing the amount of fluid which is brought into contact with the photocatalytic material. Further the arrangement of a plurality of tapered protrusions inside the reactor unit extending to a tip proximate to the radiation source creates a certain amount of turbulence to further increase the contact of air flowing through the reactor unit with photocatalytic material, whilst maintaining a low pressure loss (low resistance) on air flowing through system.

Preferably the tapered protrusions extend substantially perpendicularly from the internal surface of the catalytic material support wall portion towards the radiation source.

Advantageously having tapered protrusions around the internal surface of the reactor inside the reactor which extend substantially perpendicularly towards a central axis of the radiation source enables the surface area of the photocatalytic material on the catalytic material support that is exposed to direct ultraviolet radiation from the radiation source to be maximised.

The plurality of tapered protrusions may preferably be arranged in successive rows around the internal surface of the catalytic material support, each offset at a certain angle with respect to the previous row. Such a stepped (angularly offset) arrangement of the tapered protrusions advantageously provides effective mixing of the air flowing through the reactor unit.

Advantageously the tapered protrusions have an average height to largest base diameter ratio of 6:1 to 1:1, preferably 4:1 to 2:1. In this way the surface area of the photocatalytic material support and the distance between the radiation source and the photocatalytic material may be optimised for effective and reliable treatment.

The base portion of the tapered protrusions may have any suitable cross-section shape, for instance circular, oval, hexagonal, octagonal, rhomboid or triangular. In order to maximise the surface area of photocatalytic material exposed to direct UV light radiation the tapered protrusions preferably have an external form with flat or rounded surfaces. Advantageously the tapered protrusions may have a conical form.

Advantageously the form of the reactor unit according to the present invention permits a high air flow rate, e.g. of 20 to 100 $m^3$/h, whilst maintaining a low pressure loss e.g. less than 300 Pa.

According to a particular feature of the invention the catalytic material support is constructed from a single sheet of flexible material. The tapered protrusions are formed integrally from the sheet of flexible material and the sheet is folded to form a tubular shape.

The catalytic material support may advantageously be formed from a sheet of flexible plastics material, e.g. polystyrene, polyvinyl chloride, acrylonitrile butadiene styrene, polyethylene, polyethylene terephtalate, polymethyl methacrylate; but also a sheet of metal e.g. steel, aluminium or a sheet of mineral, vegetal or plastic fibers. The tapered portions can advantageously be easily and economically integrally formed from a sheet of flexible plastics material by moulding or thermoforming, for instance. Accordingly, no complex tool or procedure is required for the manufacture of the catalyser device.

The photocatalytic material may advantageously be applied to the catalytic material support before the support is folded to form a tube. For instance the photocatalytic material may be painted or sprayed onto the surface of the catalytic material support sheet before folding of the support to form a tube. Advantageously the photocatalytic material may be sprayed onto the catalytic material support sheet by a mechanised spraying system substantially only to the area under illumination thus reducing waste. The spraying system could be an automated spray system, making the application of the photocatalytic material to the reactor unit very simple and economic.

The photocatalytic material may be any known photocatalytic material. Advantageously the photocatalytic material may comprise an inorganic binder including ultraviolet light permeable polymeric molecules, a polar diluent, and particles of an inorganic semi-conductor, the weight of the inorganic semi-conductor particles being two to twenty times less than the weight of both the diluent and binder. The inorganic semi-conductor may be for instance cadmium sulphide, zinc sulphide and/or titanium dioxide. Preferably the photocatalytic material comprises titanium dioxide. The polymeric molecules may include acrylic molecules. Advantageously a photocatalytic gel as described in WO 2007/060520, incorporated herein by reference may be used.

Further disclosed herein is a reactor unit for photocatalytic treatment of fluids, for instance for cleaning and deodorising air, comprising a catalyser device comprising a catalytic material support having a generally tubular shape forming an air conduit and a photocatalytic material coated on at least a portion of an internal surface of the support, a housing having a tubular body with a cavity for receiving the catalyser device, a radiation source received in a central portion of the catalyser device, an air inlet module, an air outlet module and a filter comprising one or more metal components having fluid purifying activity mounted in at least one of the fluid inlet and air outlet modules.

The metal may be for instance a metal that has germicide activity, such as copper, silver or zinc or a reactive metal that has activity for converting noxious chemicals into compounds harmless to the human organism, e.g. which can act to convert carbon monoxide to carbon dioxide, such as gold, platinum, palladium, rhodium, or zirconium.

Advantageously the filter may be in the form of a foam, e.g. formed from a plastics or metallic material, with the one or more metal components having air purifying activity coated thereon.

The filter component may advantageously provide further enhanced fluid purification properties of the reactor unit, e.g. with respect to certain pathogens e.g. bacteria, and with respect to removing certain noxious compounds such as carbon monoxide.

Further described herein is a reactor unit for photocatalytic treatment of fluids, for instance for cleaning and deodorising air, comprising a catalyser device comprising a catalytic material support having a generally tubular shape forming an air conduit and a photocatalytic material coated on at least a portion of an internal surface of the support, a radiation source received in a central portion of the catalyser device, a fluid inlet module and a fluid outlet module, wherein at least one of the fluid inlet module and air outlet module comprises a radiation baffle having multiple fluid-flow passages.

The radiation baffle may advantageously comprise multiple concentric S-shaped vanes running from an axially interior surface to an exterior surface of the inlet and/or outlet modules.

The radiation baffle acts to prevent ultraviolet light emitted by the radiation source from being visible outside of the fluid inlet module and fluid outlet module reactor. Advantageously the radiation baffle effectively minimises or eliminates the direct emission of the ultraviolet light emitted by the radiation source outside the reactor unit. Accordingly the reactor unit may be used in any environment without requiring an additional cover or outer housing, making the reactor unit easy and safe to use.

Objects of this invention are also achieved by an apparatus for cleaning and deodorising air according to the claims.

There is provided an apparatus for photocatalytic treatment of fluids, for instance for cleaning and deodorising air, comprising a reactor unit as disclosed herein and a drive unit to which the reactor unit is removably connected. The drive unit comprises a power source for providing electrical power to the radiation source, and a fluid flow system for propelling or drawing fluid through the reactor unit.

Advantageously the removable connection between the reactor unit and the drive unit is provided by complimentary quarter-turn electrical connectors on the drive unit and reactor unit.

Accordingly the reactor units may be easily and conveniently attached and removed from the drive unit such that they may be easily and conveniently replaced during the life of the apparatus. The use of a quarter turn electrical connector on the reactor unit allows simple and easy connection of the reactor units into a fluid purification system.

There is also disclosed an apparatus for cleaning and deodorising large volumes of gaseous fluid comprising a plurality of the reactor units grouped together in a single unit or housing.

Advantageously the reactor unit and apparatus according to the present invention provides for effective and efficient photocatalytic treatment of fluids, for instance cleaning and deodorising of air.

Advantageously, the fact that the all of the parts of the reactor unit may be simply and economically manufactured means that the reactor unit may be easily and economically replaced. The ability to easily and economically change the reactor unit enables apparatus to have a long operation lifetime, whilst at the same time ensuring continued effective cleaning and deodorizing properties in an economic manner.

The compact and modular nature of reactor unit enables it to be easily integrated into a fluid treatment apparatus with a single reactor unit or with a plurality of reactor units, depending on the volume of fluid to be treated. The reactor units may advantageously for the purification treatment of air (cleaning, sterilising and deodorising) in various environments such as in households, offices, factories, and hospitals. The particularly compact arrangement and efficient and effective operation of the reactor unit, as well as its low weight, also enables it to be advantageously used in aircraft and automobiles for cleaning, sterilising and deodorising air.

The reactor unit may also be used for the photocatalytic treatment of many other gases or mixture of gases for various applications in industry, for example purification of nitrogen or carbon dioxide for the food and beverage industry, deodorisation of effluents, treatment of ultra pure air in electronic or pharmaceutical clean rooms.

BRIEF DESCRIPTION OF THE DRAWINGS

Further objects and advantageous aspects of the invention will be apparent from the claims and the following detailed description of an embodiment of the invention in conjunction with the drawings in which:

FIG. 4b is a detailed perspective view of a portion of the catalytic material support shown in FIG. 4a;

FIGS. 8a to 8c are perspective views of apparatus for photocatalytic treatment of gaseous fluids according to further embodiments of the present invention.

DETAILED DESCRIPTION

Figure 1:
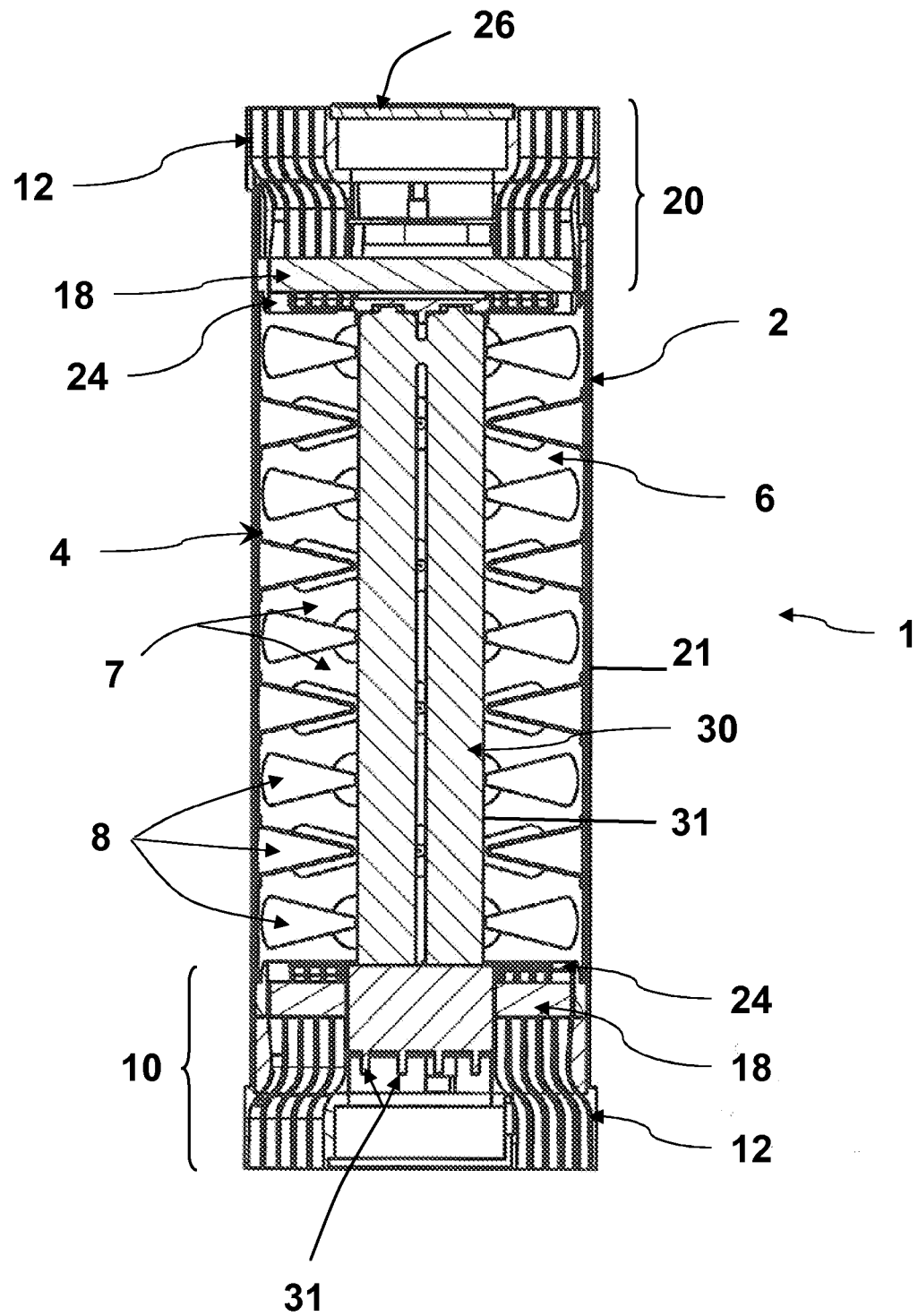
FIG. 1 is a cross-section view of a reactor unit for photocatalytic treatment of gaseous fluids according to an embodiment of the present invention.
Figure 2:
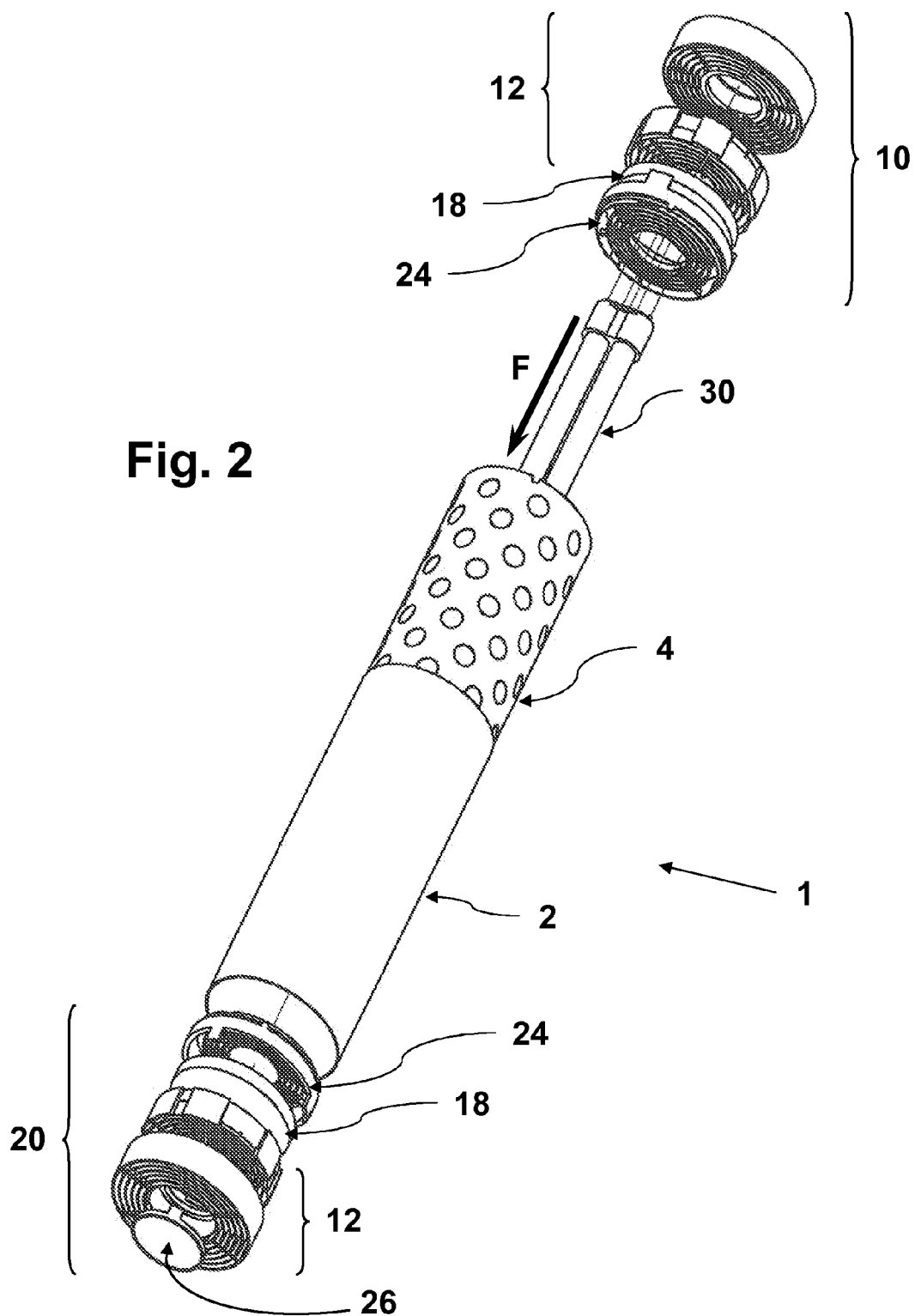
FIG. 2 is perspective exploded view of a reactor unit for photocatalytic treatment of gaseous fluids according to an embodiment of the present invention.

Referring to the figures, in particular FIGS. 1 and 2, a reactor unit 1 for photocatalytic treatment of gaseous fluids according to the present invention includes a housing 2, a catalyser device 4 removably mounted in the housing, an ultraviolet radiation source received centrally in the catalyser device, a fluid inlet module 10 and a fluid outlet module 20. It is understood that the fluid inlet module and fluid outlet module may be reversed depending on the direction of the fluid-flow through the reactor unit.

The catalyser device 4 comprises a catalytic material support 6, having a tubular shape defining a fluid flow channel extending around and along a fluid flow path. In the illustrated embodiment, the catalyser support material and the housing have a generally cylindrical shape. However, the catalytic support material and the housing may have any other generally tubular profile, such as elliptical or polygonal, depending on the arrangement of the ultraviolet radiation source and the projection of UV radiation therefrom. The tubular shape of the catalyser device preferably extends in an essentially linear general fluid flow direction F as shown in the embodiments illustrated, but could also extend in a generally curved or non linear manner (not shown).

In the embodiment illustrated in FIGS. 1 and 2 the fluid inlet module and fluid outlet module comprise the same functional units of a radiation baffle 12, a metallic filter 18 and a filter support 24. The fluid outlet 20 further includes a cover piece 26 which can be used as print support.

Referring particularly to FIGS. 1, 3a-3c, the catalytic support material 6 comprises a wall portion 7 and a plurality of tapered protrusions 8. The tapered protrusions have a base portion 5, on an internal surface 21 of the wall portion of the catalytic material support, and a tip 3 proximate to the radiation source 30.

The radiation source is preferably positioned along the central axis of the catalyser device. The ultraviolet radiation source may conveniently be one or more UV lamps, for instance a low or medium pressure mercury lamp, an incandescent lamp or a fluorescent lamp. It may have a cylindrical shape, a bulb shape or any other shape. Conveniently the radiation source may be one or more single or multiple UV tube lamps. In the illustrated embodiment the radiation source is a double tube UV lamp, which has the advantage of proving a high level of UV irradiation for a relatively short length of radiation source, and usefully allows for a single point of electrical connection.

Advantageously the ultraviolet radiation source generates light having a wavelength between 180 and 420 nm, preferably between 240 and 390 nm, e.g. 250 to 260 nm. Preferably the ultraviolet radiation source generates light having a wavelength of 254 nm. The use of ultraviolet light having a wavelength of 254 nm has been found to provide particularly effective germicide and photocatalytic activation properties. Use of light having a wavelength of 254 nm advantageously allows the production of ozone to be avoided.

The tips of the tapered protrusions may be located at a position within a range of 0 (i.e. touching the surface of the radiation source) to a distance of less than 50%, preferably less than 30%, the distance separating the surface 31 of the radiation source 30 and the internal surface 21 of the catalytic device wall portion. The tips of the tapered protrusions extend from the internal surface of the catalytic material support 7 to a position near to or touching the radiation source 30. The tips of some or all of the tapered protrusions may abut an external surface of the radiation source. The extremity of the tips of one or more tapered protrusions may be located, for instance, at a distance of 0 to 20 mm from an external surface of the radiation source, preferably 0 to 10 mm, more preferably 2 to 5 mm. The provision tapered protrusions that extend from an internal wall of the catalyser device to a position near to or touching the radiation source advantageously acts to provide a meandering non-laminar flow-path of the fluid flowing through the reactor unit, ensuring a thorough mixing of the fluid, and ensuring that all of the fluid flowing through the reactor unit is contacted with the photocatalytic material and exposed to UV radiation from the radiation source.

Preferably the tapered protrusions extend substantially perpendicularly from the internal surface 21 of the wall portion towards the radiation source 30 positioned centrally in the catalyser device, in order to avoid or minimise any areas of the internal surface of the catalytic material support that may be shaded from direct exposure to UV radiation from the radiation source. Advantageously the tapered protrusions extend substantially perpendicularly from the wall portion to a central axis of the radiation source. In this way the surface area of the catalytic material support exposed to direct ultraviolet radiation from the ultraviolet radiation source may be maximised. Where the radiation source is in the form of a plurality of UV radiation sources, e.g. a multi-tube ultraviolet lamp, the tapered protrusions positioned around the internal surface of the catalyser device may point towards a central axis where the radiation source is positioned.

Figure 3A:
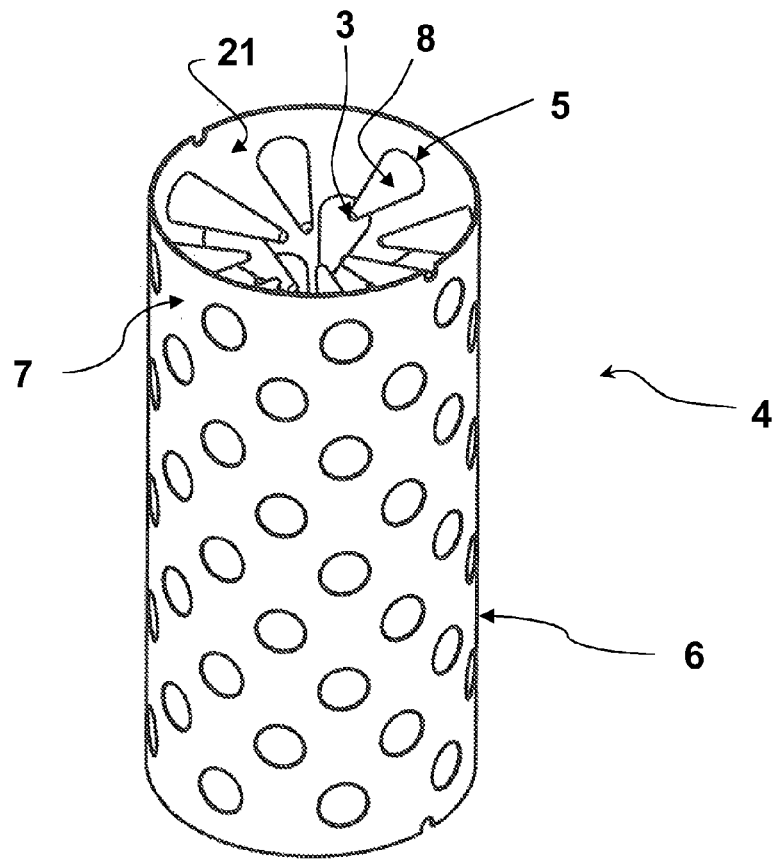
FIG. 3a is a perspective view of a catalytic device according to an embodiment of the present invention.
Figure 3B:
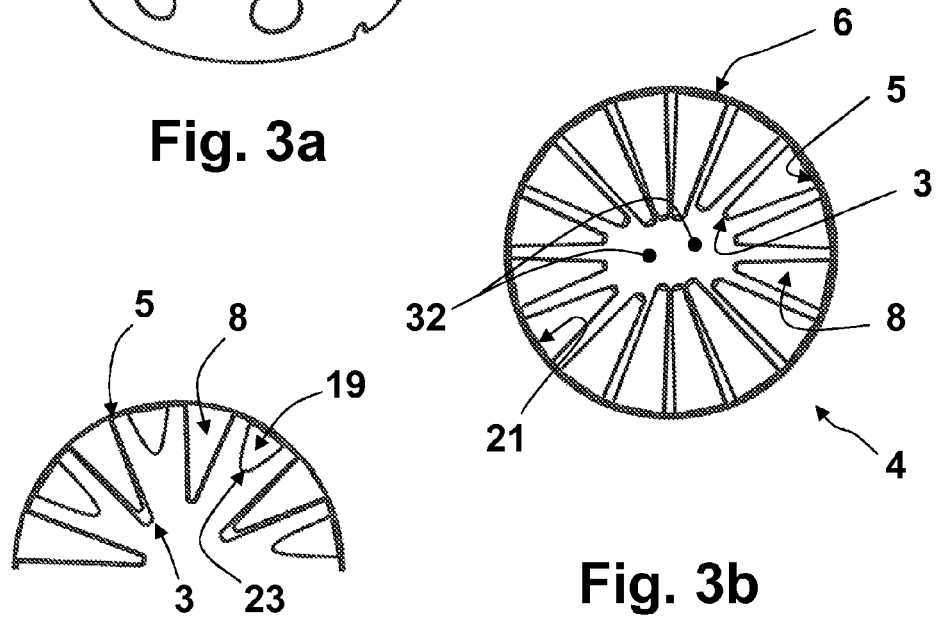
FIG. 3b is a cross-section view of a catalytic device according to the above embodiment of the invention.

FIG. 3b shows a possible arrangement of the tapered protrusions 8 around the circumference of the internal surface of a catalyser device 4 according to an embodiment of the present invention. In the embodiment illustrated the catalytic support material 6 is configured to receive a double-tube UV lamp along a central axis of the catalyser device. In FIG. 3b the tips of the tapered protrusions 8 point towards the central axis of the catalyser device which constitutes also the central axis of the double-tube UV lamp radiation source when inserted in the catalyser device. It is also envisaged that the tips of the tapered protrusions may point towards the central axis of each of the UV tubes, i.e. as indicated by the numerals 32 in FIG. 3b.

The tapered protrusions within one catalyser device may have different lengths, for instance dependant on the form of the radiation source received in the catalyser device.

Preferably the distance between the radiation source and the irradiated surface of the internal wall portion of the catalytic support material is between 20 mm to 70 mm, preferably between 30 mm to 55 mm to optimise the overall effectiveness of the photocatalytic activity on fluid passing therethrough.

The plurality of tapered protrusions may be arranged in a regular arrangement around the internal surface of the catalyser device, for instance in a series of regularly spaced rows. Preferably the tapered protrusions may be arranged in stepped rows around the internal surface of the catalytic material support, such that the tapered protrusions in each row around the circumference of catalyser device are not aligned with the tapered protrusions in the adjacent circumferential rows along the direction of fluid flow through the reactor unit. In other words, tapered protrusions at different positions along the fluid flow channel are arranged in an angularly offset manner around the internal surface of the catalytic material support. According to a preferred embodiment the tapered protrusions within a row are equally spaced apart and the rows are equally spaced along the length of the catalyser device. Preferably each row of tapered protrusions is displaced by a half step relative to the adjacent row, whereby a step corresponds to the distance between adjacent protrusions in a row. Such a stepped arrangement of the tapered protrusions advantageously provides effective mixing of the fluid flowing through the reactor unit.

Preferably the tapered protrusions 8 have a conical form, which advantageously allows a relatively natural flow of the fluid through the reactor unit and accordingly minimising the charge loss. The base portion 5 of tapered protrusions preferably has a substantially circular shape for enabling easy manufacture of the tapered protrusions. Other shapes for the base portion of the tapered protrusions may be envisaged, such as, for instance circular, oval, hexagonal, octagonal, rhomboid or triangular.

The tips of the tapered protrusion may have, for instance, a pointed, truncated or rounded form. The tips of the tapered protrusions preferably have a small cross-section area in order to minimise the surface area of the radiation source which is obstructed by the tips of the protrusions, thus ensuring that a maximum amount of the irradiation from the radiation source reaches the rest of the surface of the catalytic material support.

The tapered protrusions may preferably have an average height h to average maximum base diameter d ratio of 6:1 to 1:1, preferably of 4:1 to 2:1. The height of a tapered protrusion is here measured form the radially innermost point of the tip to the radially outermost point of the base portion. The largest base diameter is here measured as the maximum distance measured across the cross section of the base portion of the protrusion.

The tapered protrusions preferably have an internal taper angle $\alpha$ of 1 to 30°, preferably 1 to 15°, for example 5 to 15°. Accordingly, the balance between the number of protrusions within the catalyser device, providing a large surface area of photocatalytic material, and the provision of a sufficient direct irradiation of the surface of the catalyser support material by the UV radiation source may be optimised.

Figure 3C:
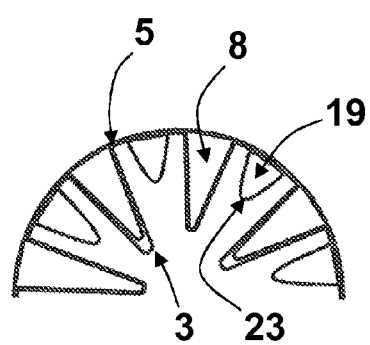
FIG. 3c is a cross-section view of a catalytic device according to another embodiment of the invention.

As illustrated in FIG. 3c, it is possible to provide in addition certain other protrusions 19 extending from the internal surface 21 of the wall portion to a tip 23 that is not proximate to the radiation source, such that the inner surface of the catalytic device comprises both long and short protrusions in view of increasing radiated catalyser surface area and to increase fluid flow contact with catalyser surface area near the base of the protrusions.

At least a portion of the internal surface of the catalytic material support is coated with a photocatalytic material. Preferably substantially the whole of the internal surface of the catalytic material support which is irradiated with ultraviolet light from the ultraviolet radiation source is coated with photocatalytic material.

The photocatalytic material may be any known photocatalytic material. Preferably the photocatalytic material comprises particles of inorganic semi-conductor, particularly, cadmium sulphide, zinc sulphide and/or titanium dioxide in anatase crystalline form. Preferably the photocatalytic material comprises titanium dioxide in view of its effective catalytic activity in the presence of ultraviolet light, its stability, and its harmlessness to the human organism.

In a particular embodiment of the present invention the photocatalytic material comprises an inorganic binder including ultraviolet light permeable polymeric molecules, a polar diluent, and particles of an inorganic semi-conductor, the weight of the inorganic semi-conductor particles being two to twenty times less than the weight of both the diluent and binder. The polymeric molecules preferably include acrylic molecules. Advantageously a photocatalytic gel as described in WO 2007/060520 may be used. Such a photocatalytic gel material exhibits good adhesion to many types of materials, and advantageously can be dried in air with out the need for high temperature treatment, thus allowing the coating of materials that do not support high temperatures such as plastics.

The photocatalytic material is applied onto an internal surface of the photocatalytic support material in order to use its photocatalytic properties to treat gases, such as clean and deodorize air. Advantageously the photocatalytic material may be in a liquid or gel form for easy application to the catalytic support material. The photocatalytic material may conveniently be applied to the catalytic material support for instance by spraying or painting of the gel or liquid on to a surface of the support, or by immerging the support into a receptacle containing the photocatalytic material.

The catalytic material support may advantageously be formed from a plastics material, e.g. polystyrene, polyvinyl chloride, acrylonitrile styrene, polyethylene, polyethylene terephtalate, polymethyl methacrylate. The tapered protrusions and the wall portion of the catalytic material support may be manufactured separately, for example by injection moulding or extrusion moulding, and bonded, welded, glued or otherwise fixed together but preferably the tapered protrusions are formed integrally with the wall portion.

Figure 4A:
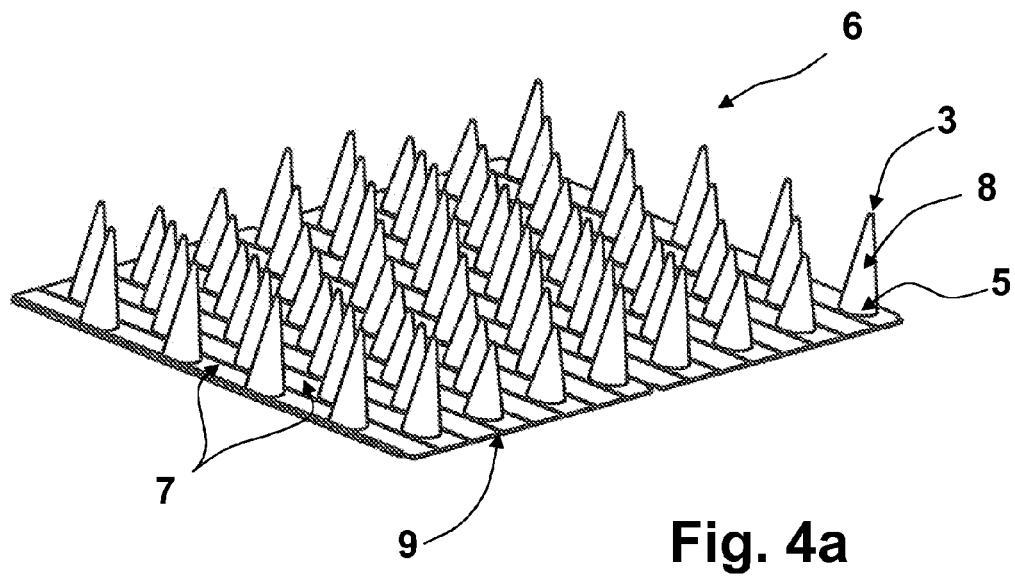
FIG. 4a is a perspective view of a catalytic material support formed from a sheet of flexible material according to an embodiment of the present invention in an unfolded state.

Referring particularly to FIG. 4*a*, according to a particular feature of the invention the catalytic material support 6 may be constructed from a single sheet of flexible material.

The tapered portions can be easily and economically integrally formed from a sheet of flexible plastics material by thermoforming or moulding or by other standard methods. The flexible plastics material may be for example polystyrene, polyvinyl chloride, acrylonitrile styrene, polyethylene, polyethylene terephtalate or polymethyl methacrylate.

Figure 4B:
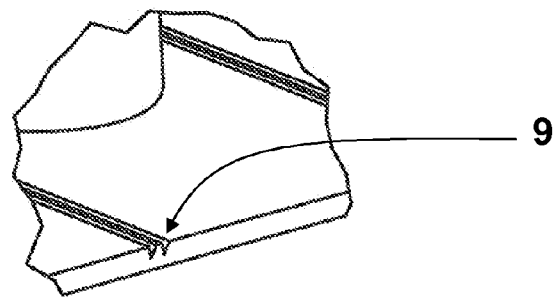
Figure 5:
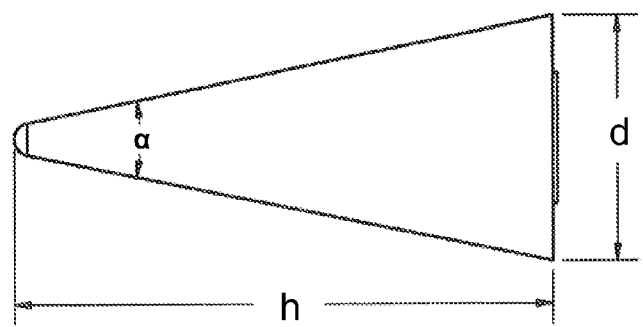
FIG. 5 is a schematic view of a tapered protrusion according to an embodiment of the present invention

The sheet of flexible material with the integrally formed tapered protrusions is then bent into a tubular shape and may be welded, crimped, bonded or held together by mechanical clamps along its seam to form a tube, or simply held in an outer support tube without being held together along its seam. The sheet may be provided with grooves or indents 9, as best seen in FIG. 4*b*, that ease the bending of the sheet into a tubular shape, and improve the reproducibility of the tubular shape.

It is preferred to form the catalytic device from a single sheet, however within the scope of the invention, it is also possible to form the catalytic device from two or more sheets welded, bonded or fixed along their edges to each other by mechanical means (such as rivets or clamps). The two or more sheets could also be assembled without being bonded together, in a tubular housing of the reactor unit that positions and supports the sheets such that they collectively form a tube around the radiation source.

The photocatalytic material may advantageously be applied to the catalytic material support before the support is folded to form a tube. For instance the photocatalytic material may be painted or sprayed onto the surface of the catalytic material support sheet before folding of the support to form a tube. Advantageously the photocatalytic material may be sprayed onto the catalytic material support sheet by a mechanised spraying system, e.g. an automated spray system, making the application of the photocatalytic material to the reactor unit very simple and economic.

Where the catalytic support material is produced from a single sheet of flexible material the tapered protrusions should be spaced sufficiently far apart to allow bending of the sheet to form a tube. The spacing required will depend, amongst other things on the diameter of the catalyser device and the relative size of the protrusions.

Where the tapered protrusions are formed integrally from the sheet of flexible material by a method such as thermoforming it is necessary that the base portion protrusions encompass a sufficient amount of the plastics material to enable the forming of the tapered protrusion. Preferably the protrusions have an average height h to average maximum base diameter d ratio 4:1 to 2:1.

The catalytic support according to the invention can thus be made particularly lightweight, while providing very efficient treatment due to the high actively radiated surface and effective aerodynamics of the tapered protrusions. This advantageously enables the reactor units according to the invention to be used in mobile applications such as in aeroplanes or automobiles, or for use in mobile or even portable fluid treatment apparatus.

The reactor unit may further comprise a radiation baffle in at least one of the fluid inlet module 10 and fluid outlet module 20, in order to prevent the ultraviolet radiation source from being visible outside the reactor unit.

Figure 6A:
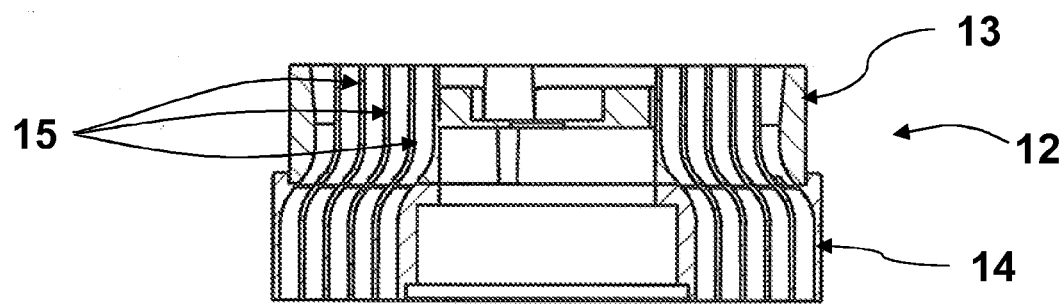
FIG. 6a is a cross-section view of a radiation baffle according to the present invention.
Figure 6B:
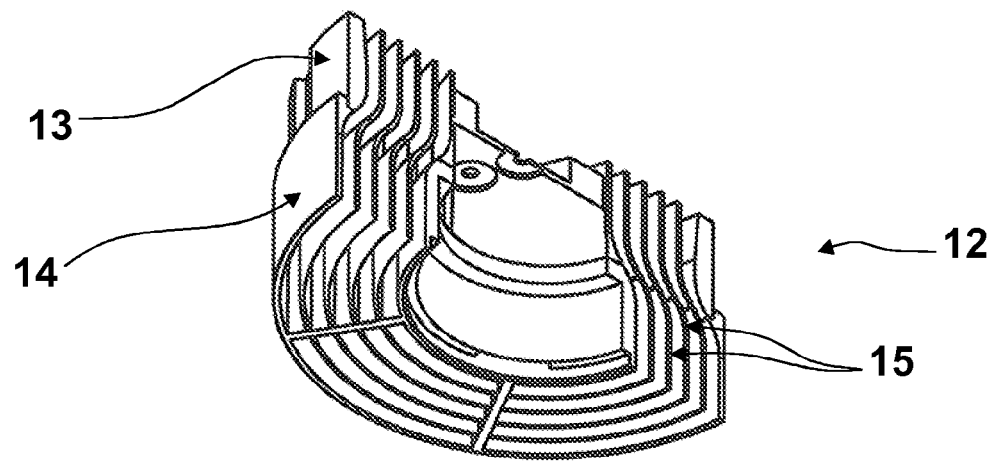
FIG. 6b is a cut-out perspective view of a radiation baffle according to the present invention.
Figure 7A:
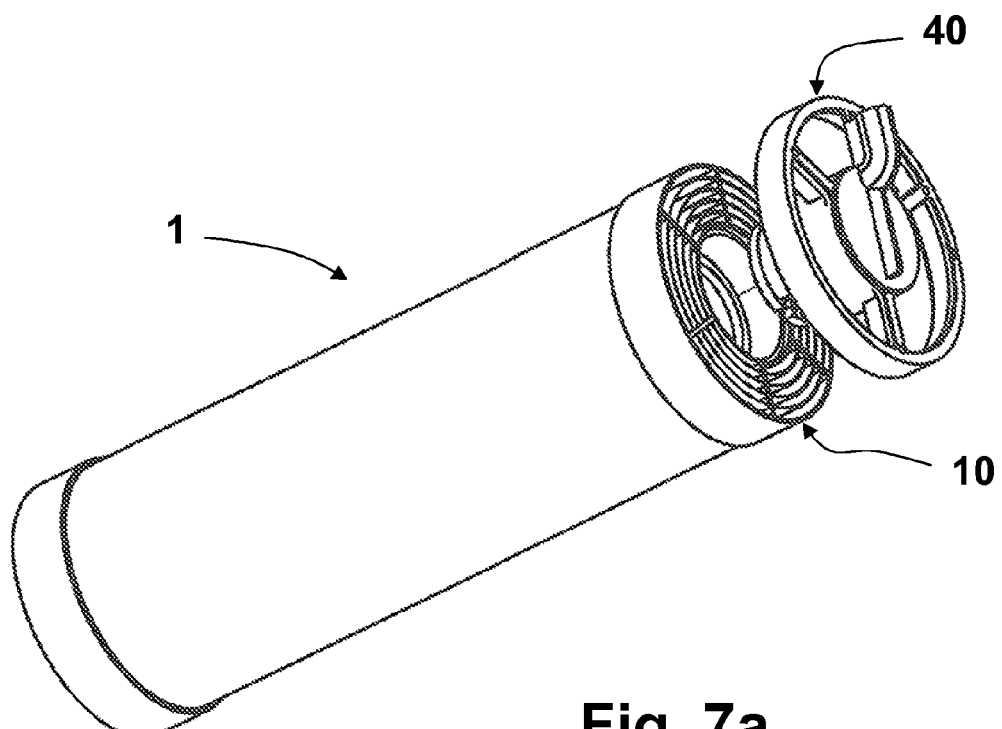
FIG. 7a is a perspective view of a reactor and a connector element according to an embodiment of the present invention.
Figure 7B:
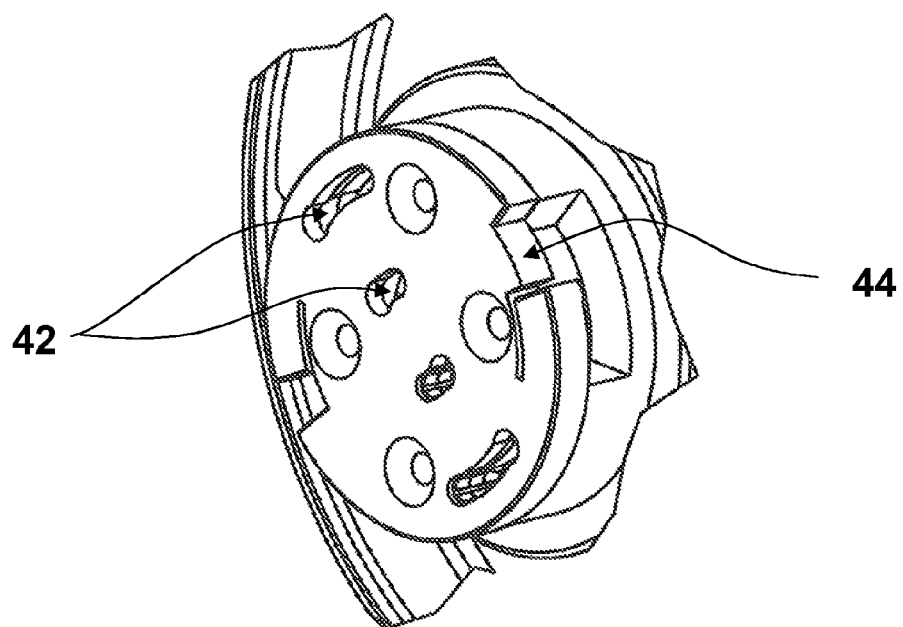
FIG. 7b is a perspective view of a connector element according to an embodiment of the present invention.

In the embodiment illustrated in FIGS. 1 and 2, the fluid inlet module 10 and fluid outlet module 20 include a radiation baffle 12 with multiple fluid-flow passages. Referring to FIGS. 6*a* and 6*b*, the radiation baffle may advantageously comprise multiple concentric S-shaped vanes 15.

The radiation baffle may be provided as a single unit. Alternatively the radiation baffle may be manufactured as separate units which may then be mounted or connected together in the fluid inlet and/or fluid outlet module. In the illustrated embodiment the radiation baffle is comprised of two separate radiation baffle units 13 and 14 which may be manufactured simply and economically e.g. from a plastics material by standard methods such as injection moulding.

The radiation baffle may conveniently be manufactured from a plastics material such as polyethylene, polybutadiene terephtalate, acrylonitrile butadiene styrene, polymethyl methacrylate, polyvinyl chloride, fibre-glass mineral or cellulosic type polymers.

Advantageously the radiation baffle effectively minimises or eliminates the direct emission of the ultraviolet light emitted by the radiation source outside the reactor unit. Accordingly the reactor unit may be used in any environment without requiring an additional cover or outer housing, making the reactor unit easy and convenient to use.

In the illustrated embodiment the radiation baffle 12 in the fluid inlet module 10 also acts as a filter to remove insects, large particles and dust. Alternatively, the reactor unit may include a separate filter at its inlet.

In the embodiment illustrated in FIGS. 1 and 2, the fluid inlet module 10 and fluid outlet module 20 comprise a metallic filter 18 to provide further improved fluid purification.

The filter comprises one or more metal components having fluid purifying activity. The metal may be a metal that has germicide activity, such as copper, silver or zinc, or a reactive metal that has activity for converting noxious chemicals into compounds harmless to the human organism, e.g. which can act to convert carbon monoxide to carbon dioxide, such as gold, platinum, palladium, rhodium or zirconium.

In the illustrated embodiment the fluid purification active metal is provided on a separate filter component 18. It is also envisaged that the metal component may be provided on the surface of a component of the reactor unit, for instance as a coating, on the surface of the radiation baffle 12.

The filter may also be formed from metal wire for instance as a gauze or fibre-glass type structure. According to a preferred embodiment the filter 18 may have an open-cell foam type structure, e.g. with at least 70%, preferably more than 80% space. Advantageously such a foam-type filter provides a large surface area of for filter for contact with the fluid flowing through the reactor unit whilst minimising charge loss. The filter may be formed from a plastics or metallic material, with the one or more metal components having fluid purifying activity coated on the surface thereof.

The metallic filter component advantageously provides further enhanced the fluid purification properties of the reactor unit, e.g. with respect to certain pathogens such bacteria, and with respect to removing certain noxious compounds such as carbon monoxide.

The reactor unit of the present invention may easily and conveniently be used in systems for air purification. FIGS. 8a to 8c show schematic illustrations of some possible air purification systems 50, 60 using the reactor unit of the present invention. The purification systems include a drive unit to which one or more reactor units according to the present invention are removably connected. The drive unit comprises an electrical connector for providing current to the radiation source electrical connector 31, and a fluid flow system for propelling or drawing air through the reactor unit. The drive unit may be configured for connection to the mains electrical network or may, for instance, be battery powered.

For instance the drive unit may include a connection member 40 with socket connectors 42 into which the electrical pin connectors of the radiation source 31 are received. Electrical connection may be effected by inserting the connection member 40 into the fluid inlet 10 or fluid outlet module of the reactor unit. Advantageously the removable connection between the reactor unit and the drive unit is provided by a quarter-turn electrical connection, whereby the connection member is inserted into the reactor unit and rotated to bring the electrical connector in the socket connectors 42 into electrical contact with the radiation source electrical pin connectors 31. The connection member or the reactor unit may comprise complimentary locking means 44 to limit the rotation of the connection member 40 with respect to the reactor unit and/or to hold the reactor unit and connection member together.

The use of a quarter turn electrical connector on the reactor unit advantageously allows simple and easy connection of the reactor units into a fluid purification system.

FIG. 8c shows an apparatus 60, designed for the cleaning and deodorising of large volumes of air or other gases according to the present invention in which may a plurality of the reactor units 1 are grouped together in a single housing 62.

The compact and modular nature of the reactor unit enables it to be easily integrated into a fluid treatment apparatus 50 having a housing 51 receiving a single reactor unit 1 or with a plurality of reactor units, depending on the volume of fluid to be treated. The apparatus housing may comprise an air inlet grill 54 and user interface screen or display 52 providing information on the usage of the apparatus and maintenance requirements, such as need for replacement of the reactor unit, radiation source and/or catalytic device.

The reactor units may advantageously be used in an apparatus for the purification treatment of air (cleaning, sterilising and deodorising) in households, offices, factories, and hospitals. The particularly compact arrangement and efficient and effective operation of the reactor unit also enables it to be advantageously used in aircraft and automobiles for cleaning, sterilising and deodorising air. The reactor unit may also be used for the photocatalytic treatment of many other gases or mixture of gases for various applications. For instance, the reactor unit may be used for purifying gases such as nitrogen or carbon dioxide used in the food and beverages industry for food preservation, deodorising gaseous effluents or treat ultra-pure air in electronic or pharmaceutical clean rooms.

The invention claimed is:

1. A reactor unit for photocatalytic treatment of fluids including a housing, a catalyser device comprising a catalytic material support being formed from a plastic material and having a generally tubular shape defining a fluid flow channel extending around and along a fluid flow path, and a radiation source received in a central axis of the catalyser device, wherein the catalytic material support comprises a wall portion and a plurality of tapered protrusions extending from an internal surface of the wall portion to a tip positioned at a distance to the radiation source within a range of 0 to 50% the distance separating the radiation source and the internal surface of the wall portion, the tapered protrusions being arranged around the central axis of the radiation source and along the fluid flow channel, and the tapered protrusions have an average height to average base diameter ratio in a range from 6:1 to 1:1, wherein the catalytic material support is in contact with the whole internal surface of the housing, and wherein the internal surface of the wall portion and the protrusions are coated with a photocatalytic material defining meandering air paths through the fluid flow channel around the central axis.

2. The reactor unit according to claim 1, wherein the tips of the tapered protrusions are within a range of 0 to 30% the distance separating the radiation source and the internal surface of the wall portion.

3. The reactor unit according to claim 1, wherein the tapered protrusions extend substantially perpendicularly from the internal surface of the catalytic material support wall portion towards the central axis.

4. The reactor unit according to claim 1, wherein the tapered protrusions have a generally conical form.

5. The reactor unit according claim 1, wherein tapered protrusions at different positions along the fluid flow channel are arranged in an angularly offset manner around the internal surface of the catalytic material support.

6. The reactor unit according to claim 1, wherein the catalytic material support is formed from a sheet of flexible plastic material folded to form a tubular shape, and the tapered protrusions are formed integrally from the sheet of flexible material.

7. The reactor unit according to claim 6, wherein the tapered protrusions are formed by moulding, extrusion or thermoforming of the sheet of flexible material.

8. The reactor unit according to claim 1, wherein the radiation source is in the form of one or more UV light tubes.

9. The reactor unit according to claim 1, wherein the housing comprises a generally tubular body with a cavity for receiving the catalyser device.

10. The reactor unit according to claim 1, further comprising a fluid inlet module, a fluid outlet module and a filter comprising one or more active metal components mounted in at least one of the fluid inlet and fluid outlet modules.

11. The reactor unit according to claim 10, wherein the filter is in the form of a plastic foam having an open pore structure coated with the active metal.

12. The reactor unit according to claim 11, wherein the active metal is selected from the group comprising silver, copper, gold, platinum, zinc, palladium, rhodium or zirconium.

13. The reactor unit according to claim 10, wherein at least one of the fluid inlet module and fluid outlet module comprises a radiation baffle having multiple fluid-flow passages.

14. The reactor unit according to claim 13, wherein the fluid-flow passages of the radiation baffle are formed by multiple concentric S-shaped vanes running from an axially interior surface to an exterior surface of at least one of the inlet and outlet modules.

15. The reactor unit according to claim 1, wherein the catalytic material support is formed from a single planar sheet of flexible plastic material bendably formed into a generally tubular shape around the central axis of the radiation source.

16. A reactor unit for photocatalytic treatment of fluids including a housing, a catalyser device comprising a catalytic material support being formed from a plastic material and having a generally tubular shape defining a fluid flow channel extending around and along a fluid flow path, and a radiation source received in a central axis of the catalyser device, wherein the catalytic material support comprises a wall portion and a plurality of tapered protrusions extending from an internal surface of the wall portion to a tip positioned at a distance to the radiation source within a range of 0 to 50% the distance separating the radiation source and the internal surface of the wall portion, the tapered protrusions being arranged to substantially surround the radiation source along the fluid flow channel, and the tapered protrusions have an average height to average base diameter ratio in a range from 6:1 to 1:1, wherein an entire outer perimeter of the catalytic material support is supported by the internal surface of the housing, and wherein the fluid flow channel is defined by the volume between the central axis and the internal surface of the wall portion less the volume of the tapered protrusions and any photocatalytic material coated thereon.

17. The reactor unit according to claim 16, wherein the catalytic material support is formed from a single planar sheet of flexible plastic material bendable formed into a generally tubular shape around the central axis of the radiation source.

18. The reactor unit according to claim 16, wherein the tips of the tapered protrusions are within a range of 0 to 30% the distance separating the radiation source and the internal surface of the wall portion.

19. The reactor unit according to claim 16, wherein the tapered protrusions extend substantially perpendicularly from the internal surface of the catalytic material support wall portion towards the central axis.

20. The reactor unit according to claim 16, wherein the tapered protrusions have a generally conical form.

* * * * *